United States Patent [19]

Kauffman

[11] Patent Number: 5,239,258

[45] Date of Patent: Aug. 24, 1993

[54] FRESHNESS AND STABILITY TEST USING OXIDATIVE DEGRADATION

[75] Inventor: Robert E. Kauffman, Centerville, Ohio

[73] Assignee: University of Dayton, Dayton, Ohio

[21] Appl. No.: 862,961

[22] Filed: Apr. 3, 1992

[51] Int. Cl.$^5$ .............................................. G01N 27/00
[52] U.S. Cl. ........................... 324/71.1; 324/444; 204/404; 204/153.1; 436/20; 436/23; 436/60
[58] Field of Search ............... 324/71.1, 71.2, 425, 324/439, 441, 444; 436/20, 21, 22, 23, 60; 204/404, 412, 153.1

[56] References Cited

U.S. PATENT DOCUMENTS

| | | | |
|---|---|---|---|
| 4,029,554 | 6/1977 | Ellison | 324/425 X |
| 4,744,870 | 5/1988 | Kauffman | 204/1 T |
| 4,764,258 | 8/1988 | Kauffman | 204/1 T |
| 5,071,527 | 12/1991 | Kauffman | 204/153.1 |
| 5,098,547 | 3/1992 | Bryan et al. | 204/412 X |

Primary Examiner—Kenneth A. Wieder
Assistant Examiner—Glenn W. Brown
Attorney, Agent, or Firm—Killworth, Gottman, Hagan & Schaeff

[57] ABSTRACT

A method for analysis of freshness of fuels, food products, and oils, lubricants and other fluids, and other organic materials, is disclosed which quickly analyzes oxidative degradation of a sample off-line by measuring the oxidation products of the material. A sample of the material is dissolved and subjected to single sweep voltammetric analysis to measure the current through the sample as a function of the potential applied. The resulting current-voltage plot reflects the level of oxidation products present in the material sampled. The method results in data which can be used to evaluate the freshness of unused materials which degrade during storage, as well as to monitor deterioration of materials during use.

24 Claims, 3 Drawing Sheets

FRESHNESS AND STABILITY TEST USING OXIDATIVE DEGRADATION

The United States government has rights in this invention, pursuant to Contract No. F33615-87-C-2714 awarded by the Department of the Air Force.

BACKGROUND OF THE INVENTION

The present invention relates generally to a method for evaluating fuels, food products and oils, and, more specifically, to a method for analyzing the freshness of fuels, food products, oils, and any organic material or foodstuff which is subject to oxidative degradation, or for which oxidative degradation is a concern.

Fuels, such as jet fuel, gasoline, diesel fuel and kerosene, are typically stored for a period before use. During bulk storage and storage in engine tanks or other use containers prior to use, fuels undergo varying degrees of oxidation. Such fuels contain substantially no natural antioxidants to prevent or control oxidation. Antioxidant additives for fuels remain in development. Accordingly, at the present time, oxidation of most fuels takes place to varying degrees. During oxidation, typically peroxides and hydroperoxides act as oxidation initiators, and lead to production of aldehydes and additional peroxides and hydroperoxides, generally referred to as oxidation products, in the fuel. Other oxidation products, such as phenols, may also be produced. If allowed to go undetected, these oxidation products will lead to gum formation and fuel line clogging.

Similarly, food products, such as milk and milk products, meat products, fish, and dried fruits and vegetables, are subject to oxidation during storage. However, most natural food products include natural antioxidants. Milk, for example, includes tocopherols, essentially vitamin E, as an antioxidant which protects its freshness. The tocopherols, as antioxidants, neutralize oxidation initiators. As the tocopherols deplete over time to low levels, the milk remains consumable. After the natural antioxidants deplete, oxidative degradation of the milk produces aldehydes and peroxides and hydroperoxides, which eventually effect the taste and result in spoilage.

Tocopherols are also present in other food products, such as fish, dried fruits, and vegetables. Meat products contain natural antioxidants such as ascorbic acid and phospholipids. To preserve freshness, artificial antioxidants are often added to food products. Butylated hydroxy toluene (BHT) and butylated hydroxy anisole (BHA) are common.

Regardless, once oxidative degradation of organic materials begins, peroxides and hydroperoxides act as oxidation initiators, and produce additional peroxides and hydroperoxides and aldehydes, which result in spoilage. The process of degradation goes further in some organic materials, particularly those subjected to thermal cycles. In those materials, aldehydes are produced as intermediate products which further oxidize to produce carboxylic acids. Once oxidative degradation begins, food products become increasingly dangerous to consume, and illness may result in varying degrees.

Oils, lubricants and other fluids are often used in ways that cause their degradation and/or subject them to thermal cycles. For example, it is common to lubricate and cool the components of operating equipment by wetting them with an oil or lubricant. As it carries out these functions, the oil or lubricant experiences various environmental stresses that cause its basestock to undergo thermal-oxidative degradation.

Oils are also used as transmission fluids and in hydraulic systems. In these uses, the oil is subjected to pressures, frequent movement, and heat. These stresses also degrade the oil.

Cooking oils are another type of oil that undergo severe thermal-oxidative stresses. The degradation of the basestock can lead to the production of aldehydes and acids, such as carboxylic acids, within the oil which affect the taste of the food.

Because of this degradation, antioxidants are frequently added to oils, lubricants and other fluids to protect their characteristics. As long as the antioxidant system remains intact, the oxidative degradation of the basestock is minimal, and so are changes in the properties.

The antioxidants in oils, lubricants and other fluids are gradually depleted over time. Eventually, the antioxidants become ineffective, allowing large changes in the physical properties of the basestock to occur. Oxidation initiators, such as peroxides, degrade to aldehydes, as in fuels and foods. The thermal input typically experienced by oils, lubricants and other fluids further cause the aldehydes in the oils, lubricants and other fluids to produce carboxylic acids, and also cause the production of phenols. At that point, the oils, lubricants and other fluids are no longer usable to protect equipment, or be consumed, and their useful lives are over. The use of an oil as a lubricant or other fluid in this condition can result in excessive component wear and eventual equipment failure.

It is undesirable to use fuels, food products, and oils, lubricants and other organic materials beyond their useful life. However, as a result of conservative precautionary measures, fuels left in storage may require premature re-refining, reprocessing or disposal. Milk and other food products may be disposed of prematurely as a safeguard, even when still consumable. Oils, for example, lubricants, have scheduled lubricant changes for various types of equipment. The length of operating time between scheduled changes is chosen very conservatively so that lubricant which is beyond its useful life does not remain in the equipment. However, these approaches result in discarding fuels, food products, oils, lubricants and other fluids which still have useful lives.

Early detection of oxidation products is important in monitoring the continued viability of fuels, food products, and oils, lubricants and other organic materials. The ability to analyze fuels, food products, and oils, lubricants and other organic materials for the presence of oxidation products, separately from, or in addition to analyzing for antioxidant depletion, would eliminate the need to reprocess or dispose of fuels, dispose of food products, or change oils on the basis of a fixed schedule. This would allow more efficient use of fuels and food products, and longer and more efficient use of oils, lubricants and other fluids, thereby providing savings in material and labor costs.

Various chemical tests and other methods have been used in the past to evaluate the oxidative degradation of fuels, food products, and oils, lubricants and other organic materials. For example, fuels are typically evaluated by subjective color tests or time-consuming chemical tests for peroxide or hydroperoxide. However, such tests, which typically test for peroxide or hydroperoxide content, are tedious, require skilled personnel, use toxic chemicals, and take up to 30 minutes to perform.

These measurements are limited to facilities with fully equipped laboratories, and consequently, are not used in the field by storage tank operators, transportation companies, and end-users of the fuel. Thus, deterioration of the fuel can continue undetected, resulting in gum formation and fuel line clogging.

Milk products have been tested chemically for aldehydes, or subjectively for taste. Other foods have been tested chemically for peroxides, hydroperoxides, carboxylic acids, and other products of oxidative degradation.

Oils, lubricants and other fluids have been chemically tested for carboxylic acids. By way of further example, for oils, lubricants and other fluids, various thermal-oxidative and chemical-oxidative stressing techniques are known which permit evaluation of remaining useful life. However, most of these techniques are also unsuitable for routine use. Thermal-oxidative stressing techniques for oils require the use of high temperatures and pressures and relatively long analysis times, about 30 minutes. Chemical-oxidative stressing techniques for oils are difficult in operation, require unstable reagents, and require even longer analysis times, up to two hours.

More recently, new approaches to testing have been developed and disclosed in U.S. Pat. Nos. 4,744,870, 4,764,258 and 5,071,527 to Kauffman. Assigned to the same assignee as the present invention, these patents disclose methods for determining the remaining useful life of oils which are fast, very accurate, easy to operate, and which can be performed with inexpensive equipment. These methods approach the measurement of useful life by measuring the amount of antioxidant remaining in oils, lubricants and other fluids. In these methods, samples are mixed off-line with a solvent, an electrolyte, and either an organic base or a solid substrate, depending on the type of oil, lubricant or fluid to be tested. The sample is placed in an electrolytic cell and subjected to a cyclic voltammetric analysis. The current generated by the antioxidants and other electroactive species during the cyclic voltammetric analysis is measured and recorded. The remaining useful life for the lubricant is then determined from the oxidation or reduction wave height.

The methods of the U.S. Pat. Nos. 4,744,870 and 4,764,258 patents can only be performed off-line, and are limited to oils or lubricants containing antioxidants. The methods of the U.S. Pat. No. 5,071,527 patent may be performed off-line or on-line, and may be used to perform analysis of antioxidant depletion, peroxide or hydroperoxide level (oxidation initiators), and carboxylic acid level (final oxidation products), but is also limited to the analysis of oils, lubricants and fluids.

In sum, these rapid, straightforward, and more recent methods are able to measure antioxidant depletion prior to oxidative degradation, and some final oxidation products produced by thermal-oxidative processes experienced during use. However, these methods lack the sensitivity to detect very low antioxidant levels and are unable to measure oxidation products of a wide range of stored materials in the early stages of oxidative degradation, while such materials are still usable or consumable.

Therefore, there remains a need for a method which can be used to quickly and accurately test for the initial oxidation products of a wide range of materials including fuels, food products, as well as oils, lubricants and fluids, to determine the freshness of the materials after storage, and to determine if continued use of used materials is possible.

SUMMARY OF THE INVENTION

The present invention solves this need by providing a method for analysis of oxidative degradation of fuels, food products, and oils, lubricants and other organic materials, which method is performed off-line. The method can be used to measure oxidation products of unused materials which degrade during storage, rather than from use. Further, the method can be used to monitor the deterioration of materials during use, such as oils, by measuring oxidation products of the material, rather than remaining antioxidant levels, to assess the viability of used oils.

The present invention is, therefore, sensitive to the initiation of oxidative degradation in materials which have no or low anti-oxidant levels, or those in which antioxidant levels are depleted to levels below detection limits of existing methods. Thus, freshness and continuing usefulness of fuels, food products and oils may be determined with ease and greater sensitivity.

Analysis of the oxidation products of materials in accordance with the present invention compliments the methods of the other Kauffman patents (U.S. Pat. Nos. 4,744,870, 4,764,258 and 5,071,527), and can be combined therewith to more completely assess the condition and usefulness of materials containing antioxidants.

The same instrumentation as used for off-line sampling, disclosed and discussed in the Kauffman patents may be used in accordance with the present invention. By contrast with the earlier Kauffman patents, however, the present invention requires different sample preparation in which solvents and procedures are employed to achieve a different result, and applies different voltage ranges for single sweep analysis to test for oxidation products in a much broader range of materials. Those materials may include, without limitation, fuels, food products, oils, lubricants, and organic materials subject to oxidative degradation. Typically, the present invention tests for the presence of aldehydes, peroxides, hydroperoxides, phenols and carboxylic acids, or combinations thereof, which are present as oxidation products in such materials.

In accordance with the method of the present invention, a sample from a supply of material is dissolved with a solvent suitable for dissolving the material and its oxidation products to produce a sample to be analyzed. Every effort is made to select a solvent, such as an alcohol or a ketone, which will dissolve both the sample and its oxidation products into solution. The method of the present invention includes applying an electrical potential of a first value with an electrode to produce an electrical current through the dissolved sample of the material to be tested. Preferably, the potential is varied in a single sweep from the first value to a second value, producing an oxidation reaction of the oxidation products present due to oxidative degradation of the material. Anodic current produced in the cell is measured and recorded. These steps of applying potential in a single sweep, and recording measured current essentially constitute a voltammetric evaluation of the material.

The position and size of the resulting current waves and peaks in the oxidation trace produced by the single sweep analysis are then used to determine the freshness of the material. The step of measuring and recording may, thus, further include comparing the readings against reference values to evaluate freshness and continuing use and viability.

Testing for oxidation products in supplies of stored or unused materials, such as fuels, food products and other organic materials subject to oxidative degradation, permits freshness of important materials to be evaluated. The further measurement of such oxidation products in materials during use, such as oils, makes monitoring of useful life even more precise. The small sample size required makes the method suitable for field use, for example at airports, storage facilities, food packaging plants and tank farms, as well as for laboratory use in refineries, food processing plants, and other production facilities.

Thus, the freshness of incoming raw materials and outgoing products may be monitored and for example, the quality of food stocks can be maintained at levels which are safe for consumption. Milk, for example, can be analyzed for aldehyde production, and consumption or use of sour milk may be avoided.

As well, the freshness of fuels may be determined to prevent the use of unstable fuels wherein aldehydes, peroxides and hydroperoxides, and phenols may cause gum formation and fuel line clogging. Thus, for example, interruption of fuel flow to aircraft engines may be avoided, potentially preventing engine malfunction and saving lives.

The continuing use of oils, lubricants or other fluids, whose antioxidant levels are below detection limits of other methods, may also be assessed. Continued monitoring and measurement of oxidation products during use may be of value in extending the period of use after depletion of antioxidants, particularly when combined with existing methods for measuring antioxidant levels. Among the advantages of such analytical results are not only extended useful lifetime of oils, lubricants, and other fluids, but the elimination of scheduled lubricant changes, and the detection of abnormal operating conditions which accelerate oil degradation prior to severe wear and equipment failure in lubrication systems, or cooking systems. Thus, for example, in the case of aircraft turbine engines, the capability of the present method to detect that the engines are experiencing severe oil degradation can potentially prevent disastrous failures and save lives.

Accordingly, it is an object of the present invention to provide a method for analyzing the freshness and stability of a wide range of materials subject to oxidative degradation, which is fast, easy to perform, and which can be used off-line. It is another object of the invention to provide a method which permits monitoring of final or intermediate oxidation products such as aldehydes, peroxides and hydroperoxides or combinations thereof. It is another object of the present invention to provide a method for testing for oxidation products and determine the freshness and stability of materials subject to oxidative degradation in storage, as well as in use. It is another object of the present invention to provide a method for testing the oxidative degradation, and remaining freshness and stability, of materials after depletion of antioxidants therein. It is another object of the present invention to provide a method for testing the freshness and stability of fuels, food products, and oils, lubricants and other organic materials subject to oxidative degradation. Other objects and advantages of the present invention will be apparent from the following description, the accompanying drawings, and the claims.

DETAILED DESCRIPTION OF THE PREFERRED EMBODIMENT

The method for analyzing materials subject to oxidative degradation, such as fuels, food products, oils, lubricants, or other organic materials, in accordance with the present invention, is based upon voltammetric analysis of a sample of the material. In general, voltammetric techniques are electroanalytical methods wherein electrodes are placed in the sample to be tested. Data is obtained by measuring the current passing through the sample as a function of the potential applied, and test results are based on current, voltage, and time relationships at the cell electrodes.

Figure 1:
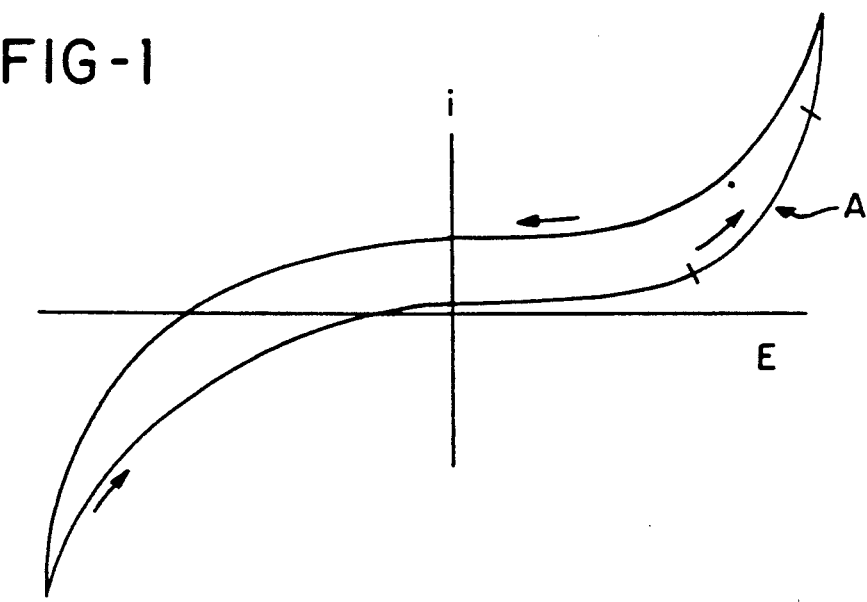
FIG. 1 is a current trace produced in a typical solvent subjected to cyclic voltammetric analysis, illustrating the area of interest for single sweep voltammetric analysis in accordance with the present invention.

In performing a voltammetric analysis, the potential across the electrodes is varied linearly with time, and the resulting current is recorded as a function of the potential. In accordance with the present invention, an initial potential applied to the electrodes of first value E1 is linearly increased over time to a second value E2. The voltage scan rate can be any rate, but is preferably 1 V/sec. A variation of this technique, known as cyclic voltammetric analysis, has been used in the earlier Kauffman patents, where the potential is varied over time through a complete cycle. Cyclic voltammetric analysis of a typical solvent, demonstrating both oxidation and reduction thereof, is illustrated in FIG. 1. The solvent includes an electrolyte to facilitate electrical conduction. The voltammetric analysis of the present invention, illustrated in FIG. 2, is preferably conducted in a single sweep over a portion of the curve in FIG. 1 designated by A.

While a cyclic voltammetric analysis can be performed in accordance with the present invention to measure the oxidation products of the sample material, a single sweep is preferred. Returning the potential from E2 to E1 has several drawbacks. During the initial sweep from E1 to E2, certain of the oxidation products, such as aldehydes and phenols, which are oxidized, also polymerize. This reaction is not entirely reversible when the potential is reduced to complete the cycle from E2 to E1, and sensitivity to the desired measurement is lessened. As well, certain of the polymerized oxidation products tend to foul the electrodes when the potential is returned to E1. Thus, a single sweep analysis is preferred.

Figure 2:
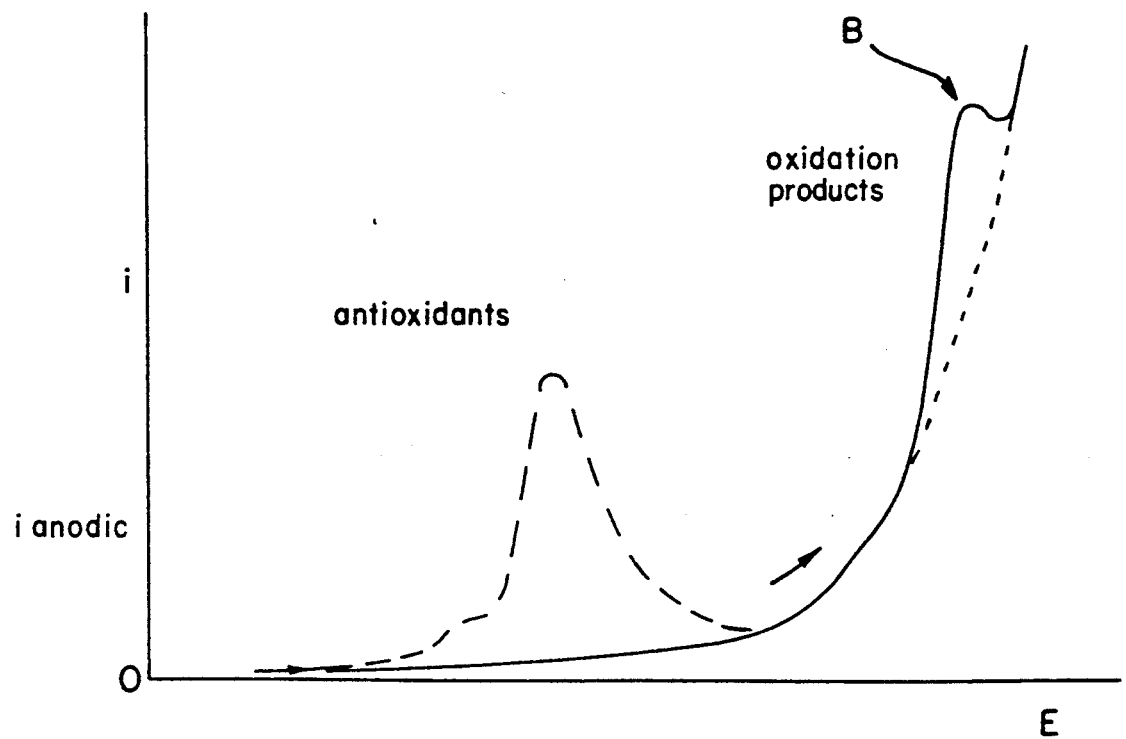
FIG. 2 is a typical current trace produced in a typical sample evaluating oxidation products of the sample material in accordance with the present invention.

Referring to FIG. 2, a typical current-potential curve produced during the practice of the present invention can be seen. As indicated by the solid line, as increasing potential is applied to the sample, an electrochemical reaction causes the oxidation products of the sample material to oxidize. Concurrently, the solvent begins to oxidize, shifting the baseline of the current trace, so that the peak produced by the sample material appears as a wave, indicated at B. The underlying solvent oxidation is indicated by a dotted line. Ultimately, as the applied potential increases still further, the oxidation reaction of the solvent overwhelms that of the oxidation products of the sample material. The data recorded during the oxidation reactions can, thereafter, be used to determine the freshness of the material.

As further shown by dashed lines in FIG. 2, where an antioxidant species is present in the dissolved sample, the applied potential produces an electrochemical reaction therewith to produce an oxidation wave. This type of reaction was the focus of the previous Kauffman patents. See, for example, U.S. Pat. No. 4,764,258. However, the present invention is capable of determining the freshness of a sample lacking antioxidants, and the presence or absence of antioxidants is irrelevant.

Once the voltammetric analysis has been performed, the results are analyzed. The position of the wave, the maximum peak, the height of the peak, and/or the area under the peak minus the baseline shift due to the solvent, are compared to data previously taken. The level of oxidation products present in the sample reflect the freshness of the material from which the sample was taken, and the suitability of the material for use, continued storage, or continued use may be determined. The exact amounts or levels which are relevant to freshness will depend upon the type of material which is being evaluated. These values can be determined through prior, controlled testing of the material.

Controlled testing of materials can be undertaken to determine reference values in accordance with the method of the present invention for various levels of freshness. For some materials, aging occurs over a sufficiently short time that reference values are easily developed. For other materials, aging occurs slowly, and various methods may be used to simulate aging. The materials of simulated age may then be sampled in accordance with the present invention to determine reference values for various levels of freshness. For example, oxidative degradation in fuels may be simulated by thermal stressing techniques which accelerate the natural oxidation process. As a general rule, the rate of oxidation in fuels will double with each 10° C. rise in temperature. Thus, many months of aging may be simulated in a days time if sufficient temperature is applied. Generally, aging of organic materials may be accomplished by ASTM methods D2274 and D4625-86 performed at 95° C. and 43° C., respectively, and have been correlated with long term, room temperature stability tests.

The instruments used for voltammetric analysis preferably comprise a working electrode, a reference electrode and an auxiliary electrode, and lead(s). The working, reference, and auxiliary electrodes may be made from any material which is conductive. However, glassy carbon is preferred for the working electrode, and platinum is preferred for the auxiliary and reference electrodes.

The method of the present invention will now be illustrated by reference to several examples in which analyses of sample materials are detailed. The method is not intended to be limited to the specific, exemplary materials but, rather, may be practiced generally with a broad range of materials, as further indicated by the general example, Example 4, discussed below.

EXAMPLE 1

Aviation fuel

Figure 3:
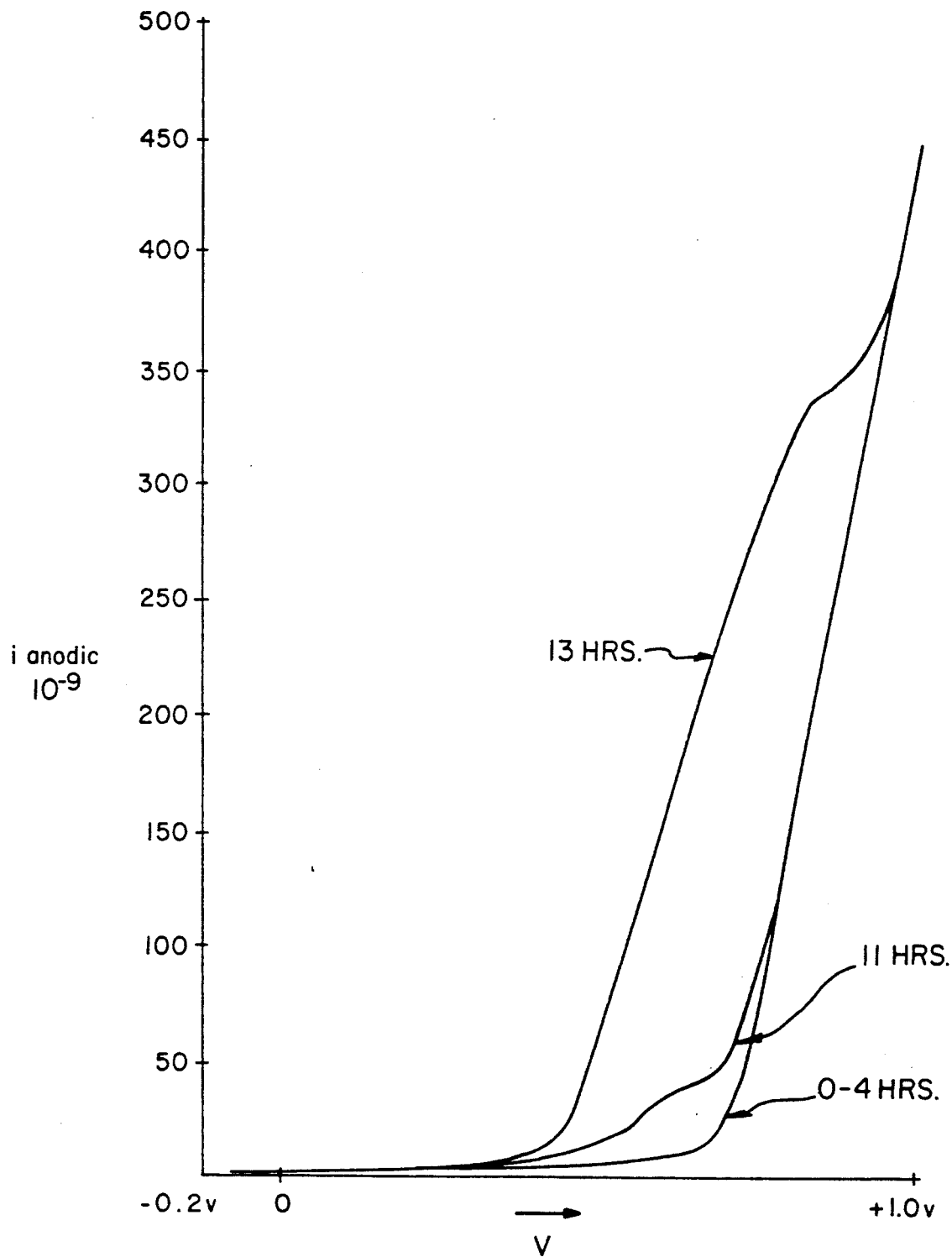
FIG. 3 is a plot of a series of current traces produced in aviation fuel to evaluate the oxidation products of the aviation fuel at different stages of oxidative degradation in accordance with the present invention.

FIG. 3 shows a series of current-voltage plots produced in accordance with the present invention, reflecting the presence of oxidation products in aviation fuel at different stages of oxidative degradation. Samples were taken from a 24-hour fuel oxidation test which heated the fuel to approximately 160° Centigrade (° C.) to stress and simulate aging of the fuel in storage at 70° F. over a period of months.

Samples of the fuel were prepared for analysis by mixing 0.1 milliliters (ml) of fuel with 2 ml of isopropanol (a solvent), and 0.1 ml of aqueous tetraethylammonium hydroxide (25%) solution (as an electrolyte), in a 5 ml sample vial. The vial was capped and the solution was then shaken by hand for approximately 2 seconds. The voltammetry electrode system was thereafter inserted and a single sweep voltammetric analysis was made from approximately −0.2 volts (V) to 1.0 V (referenced to platinum).

The peak heights and position of the resulting current waves are shown in FIG. 3. The curves may be used to monitor the oxidation of the fuel supply. As may be seen, during the first four hours of testing (representing approximately 3 months of storage at 70° F.), the aviation fuel is stable, and no oxidation products are detected. The monitored oxidation products then increase in concentration between 4 and 13 hours (representing approximately 9 months) of stressing. Between 13 and 20 hours (representing approximately 14 months of aging), the oxidation products (not shown) decrease to a steady state concentration, which is obtained after about 20 hours of stressing.

The degree of oxidation may be determined both by the peak height of the resulting current waves relative to the blank or to the 0 to 4 hour curve, and by the position along the voltage axis of the plot at which the current trace begins to curve or deviate upward. This latter factor permits distinguishing curves generated by fuel which has experienced between 11 and 13 hours of stressing (i.e. approximately 8 to 9 months of aging), from fuel which has experienced from 13 to 24 hours of stressing (i.e. approximately 9 to 17 months of aging), (not shown). After 11 hours of stressing (approximately 8 months of aging in storage) the aviation fuel is generally unusable due to the level of oxidation products, such as aldehydes, hydroperoxides, acids produced by hydroperoxide decomposition, and phenols. Conventional, subjective color tests of the fuels can qualitatively verify that the fuel has degraded and become unstable and unusable. However, as the fuel in FIG. 3 remains colorless up to 13 hours of stressing, such verification typically comes too late.

Early detection of oxidation in aviation fuels is necessary because of the critical consequences of fuel line clogging in aircraft. Further, advanced engine designs are being developed in which fuels experience elevated temperatures prior to use, accelerating aging and making the freshness of fuels more critical. Due to aging, strategic stockpiles of stored aviation fuels are routinely disposed of and wasted, rather than monitored and used before reaching the end of their useful lives. Conventional tests detect the effects of oxidation in such fuels too late in the process. As may be seen, the method of the present invention produces results which are sensitive to initial oxidation of such aviation fuels, and may be used to monitor the oxidative degradation of fuels. The present invention has been found to be more sensitive than commonly used monitoring techniques such as color, total acid measurements, and conductivity measurements. Moreover, the present invention is safer to use, more rapid, and easier to operate than conventional peroxide monitoring techniques which employ toxic chemicals.

EXAMPLE 2

Milk

Figure 4:
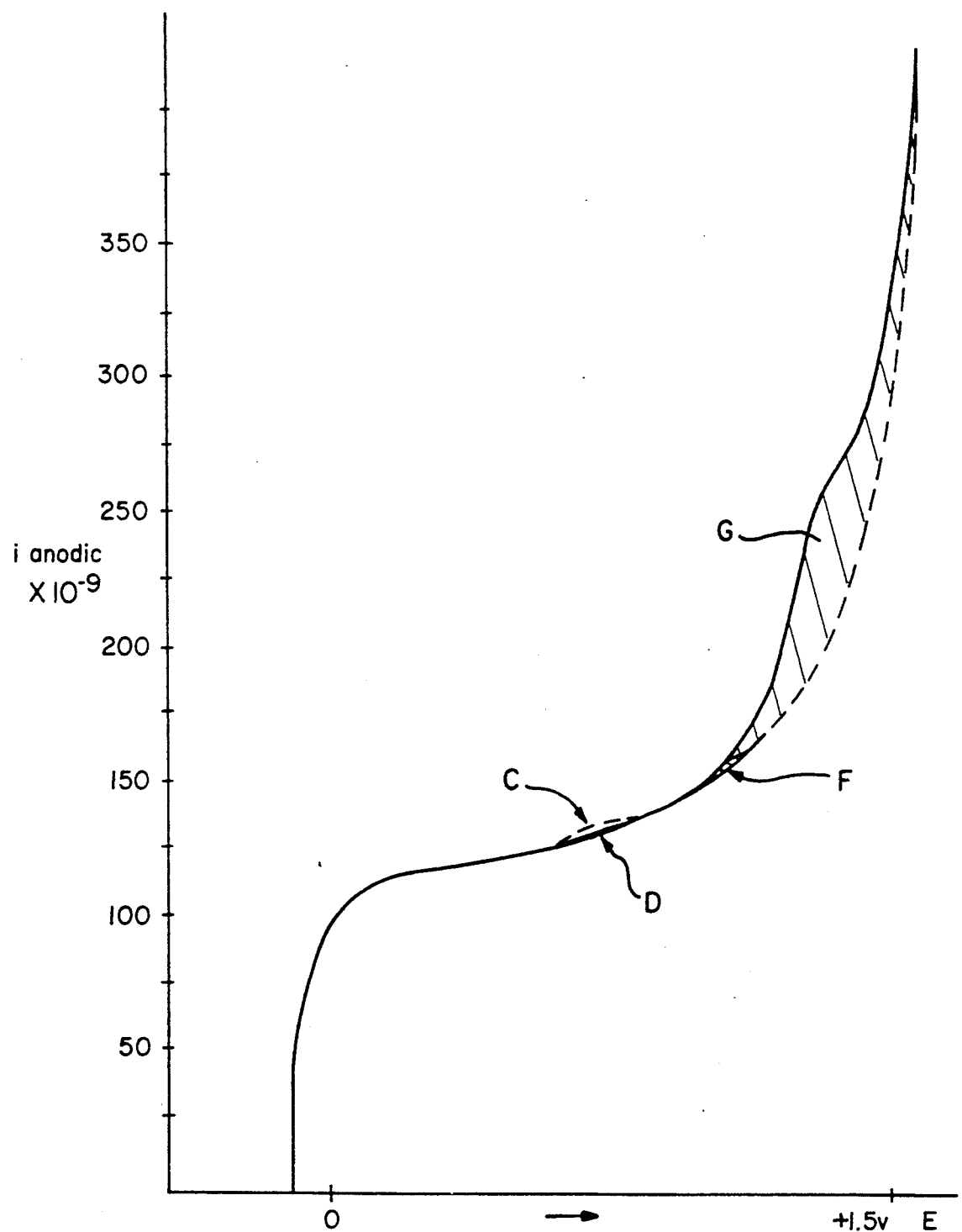
FIG. 4 is a plot of current traces produced in fresh and sour milk to evaluate the oxidation products of the milk in each state in accordance with the present invention.

FIG. 4 shows two current-voltage plots superimposed on each other, which were produced in fresh and sour milk in accordance with the present invention to evaluate the oxidation products of the milk in each state. The fresh milk is shown in a dashed line, where the plot varies from that of the sour milk, shown in solid line. The plot for the fresh milk serves as a blank or reference. The sour milk sample was taken from a supply of milk which was stored at room temperature for one week.

Samples of the milk were prepared by mixing 0.2 ml of milk with 2 ml of isopropanol (a solvent) having 0.2 Moles (M) of $LiClO_4$ (as an electrolyte) in a 5 ml sample vial. The vial was capped and the solution was then shaken by hand for approximately 2 seconds. The voltammetry electrode system was thereafter inserted, and a single sweep voltammetric analysis was made from approximately 0.0 V to $+1.5$ V (referenced to platinum).

Again, the peak heights and position of the resulting current waves shown in FIG. 4 are used to monitor the oxidation of the milk supply, and may be used as reference curves for comparison with unknown samples. The waves in FIG. 4 are also plotted against an ideal reference blank, which demonstrates that each plot has two features. A natural antioxidant is detected in the fresh milk at C which can be seen to deplete with storage at room temperature, as shown at D. Due to the low sensitivity of the voltammetric technique to the antioxidant species in the milk, the use of antioxidant measurements to measure the freshness of milk would be impractical. In contrast to the antioxidant species, the oxidation product accumulation in the sour milk, seen at G, is very easily measured in accordance with the method of the present invention. In fact, minimal amounts of the oxidation products are already detected in the fresh milk sample, as indicated at F, demonstrating the sensitivity of the method of the present invention.

Development of FIG. 4 to include additional plots for milk at different stages of oxidative degradation may be accomplished in accordance with the method of the present invention to provide a complete reference for use in determining the freshness of unknown samples and their suitability for consumption or use.

The current waves in FIGS. 3 and 4 may be used as reference values for comparison against current-voltage plots for unknown samples. Curves representing other intermediate levels of oxidative degradation may also be developed in accordance with the method of the present invention. Comparisons of unknowns to reference values may be further facilitated by plotting and comparing the derivatives of such curves.

It is also noted that with regard to fuels and milk, as well as other materials tested in accordance with the present method, different solvents and electrolytes can be used. For example, for fuel and milk, solvents other than isopropanol can be used. Other alcohols, such as methanol and ethanol, water, and various ketones have been used with different degrees of success. Similarly, various electrolytes can be used.

EXAMPLE 3

Other Organic Materials

The method of the present invention is applicable to a broad range of organic materials including fuels, food products, oils, lubricants, and other organic materials subject to oxidative degradation. Different materials in this broad range of materials will require different solvents, as necessary to dissolve the material sample and its oxidation products as completely as possible, into solution. As well, different electrolytes may be used, as necessary, to reduce the resistivity of the sample solution.

The choice of solvent and electrolyte may be made by trial and error by one skilled in the art to achieve a workable sample. The sample/solvent ratio to be used is dependent on the sensitivity of the test to the species of interest, and the sensitivity desired. Generally, the higher the sample/solvent ratio, the higher the sensitivity.

Any solvent capable of dissolving the sample and electrolyte (if required) can be used. Solvents may be, for example, alcohols, such as methanol, ethanol, isopropanol or propanol; ketones, such as methyl ethyl ketone or acetone; or water.

Any soluble electrolyte can be used, and is preferably at minimal concentrations required to overcome resistivity to current flow. The concentrations used in Examples 1-2 may be instructive as starting points. Electrolytes may be, for example, lithium perchlorate; tetralkylammonium perchlorate; or a base, such as potassium hydroxide or tetralkylammonium hydroxide.

Once an appropriate solvent and electrolyte are chosen, the range of applied potential may be determined by performing a voltammetric analysis of the solvent and electrolyte as a blank to determine at which voltage level the solvent blank is overwhelmed by current. Typically, in carrying out the voltammetric analysis, the potential is varied in a range between approximately $+3$ V and approximately $-3$ V. Measured current flows are typically in the range of microamperes, and may be measured in nanoamperes.

Once the sample/solvent ratio, solvent, electrolyte (if needed), and voltage range parameters are determined, the method of the present invention may be performed on test samples having known levels of freshness to calibrate the instrument readings. The samples are preferably prepared as in Examples 1 and 2, in similar sizes. Further, the vials are capped and then shaken by hand for approximately 2 seconds. Again, the voltage is to be applied, preferably at approximately 1 V/second, to the point where the oxidation reaction of the solvent overwhelms the sample. The temperature of the known samples should be representative of the temperature of samples which will be tested.

In accordance with above, a series of current waves for a material at known stages of oxidative degradation may be developed in accordance with the method of the present invention for use as reference values. Comparison of these current-voltage plots, or the derivatives thereof, can be made against similar plots for unknowns.

Thus, finally, samples of unknown age may be analyzed in accordance with the present invention, and their freshness determined. The continued use and viability of the material may then be confirmed.

Where samples are from materials also having antioxidants, the degree of oxidative degradation may be determined in accordance with the method of the present invention, and the antioxidant level may be determined in accordance with the earlier Kauffman patents to enable the user to make a more complete assessment of the useful life and usability of a fluid.

Where a material having antioxidants, such as lubricating oil, is tested in accordance with Example 3 above, the current wave which results from the method of the present invention will typically resemble that of FIG. 2, further reflecting the presence of antioxidants, shown by a dashed line. As the lubricating oil ages, current waves reflecting the increasing accumulation of oxidation products will be seen, while the curve reflecting the antioxidants disappears. The measurement of oxidation products in accordance with the present invention permits further monitoring and use of the oil after the antioxidants are depleted, allowing extended lubricant life, without causing engine or equipment failures. The current waves will reflect the level of oxidation products, such as aldehydes, hydroperoxides, acids produced by hydroperoxide decomposition, carboxylic acids and phenols, which ultimately render a lubricating oil unusable. Detection of oxidative degradation in lubricating oils after antioxidant depletion is desirable because of the expense and dangers of engine failures. As may be understood, the method of the present invention will produce results which are sensitive to oxidation after antioxidants have been depleted, allowing extended life.

The present invention can be used to monitor the oxidative degradation of many materials for numerous different applications. Such materials, without limitation, may include. fuels, such as aviation fuels, automotive fuels, diesel fuels, and kerosene for many different applications such as engines, lamps, heaters and stockpiles; food products, such as milk, dried fruits and vegetables, fish and meats for human or animal consumption or use in various processes; oils, lubricants, and fluids for many other applications, for example, gas turbine engines, combustion engines, transmission systems, hydraulic systems, gear boxes, operating machinery, and deep fryers such as those frequently used in restaurants; and other materials, such as organic materials, subject to oxidative degradation. Other uses will be apparent to those skilled in the art.

While certain representative embodiments and details have been shown for purposes of illustrating the present invention, it will be apparent to those skilled in the art that various changes in the method disclosed herein may be made without departing from the scope of the invention, which is defined in the appended claims.

What is claimed is:

1. A method for measuring the freshness and stability of a supply of material subject to oxidative degradation producing at least aldehydes or phenols, comprising the steps of:
   bringing electrodes into contact with a sample of material from a supply subject to oxidative degradation to measure at least the aldehyde and phenol oxidation products of the material;
   applying an electric potential of a first value to the sample to produce an electric current therethrough;
   varying the potential in a single sweep from the first value to a second value to produce an oxidation reaction in at least a portion of said aldehyde and phenol oxidation products; and
   measuring and recording the current during said oxidation reaction.

2. The method of claim 1 wherein said electrodes include a working electrode, a reference electrode, and an auxiliary electrode.

3. The method of claim 1 wherein said supply of material subject to oxidative degradation is selected from the group consisting of fuels, food products, animal or plant products, products using animal oils, products using vegetable oils, oils, or lubricants.

4. The method of claim 1 wherein said first and second potential values are in the range of $+3.0$ V and $-3.0$ V.

5. The method of claim 1 wherein the step of bringing electrodes into contact with a sample includes the steps of:
   substantially dissolving material from said supply in a solvent in which at least the aldehyde and phenol oxidation products of said material are also soluble, to produce a sample; and
   dissolving an appropriate additive in said sample to reduce the electrical resistance thereof, wherein said additive comprises an electrolyte or base.

6. The method of claim 5 wherein said solvent is selected from the group consisting of alcohols, ketones and water.

7. The method of claim 6 wherein:
   said alcohols are selected from the group consisting of methanol, ethanol, isopropanol, and propanol; and
   said ketones are selected from the group consisting of methyl ethyl ketone and acetone.

8. The method of claim 5 wherein said electrolyte is selected from the group consisting of lithium perchlorate and tetralkylammonium perchlorate.

9. The method of claim 5 wherein said electrolyte comprises a base.

10. The method of claim 9 wherein said base is selected from the group consisting of potassium hydroxide and tetralkylammonium hydroxide.

11. The method of claim 5 wherein said supply of material is a supply of fuel, said solvent is selected from the group consisting of a neutral electrolyte and isopropanol, and said electrolyte or base is selected from the group consisting of potassium hydroxide and an aqueous solution of tetraethylammonium hydroxide.

12. The method of claim 11 wherein said first and second potential values are approximately $-0.2$ V and $+1.0$ V.

13. The method of claim 5 wherein said supply of material is a supply of milk, said solvent is selected from the group consisting of a neutral electrolyte and isopropanol, and said electrolyte or base comprises lithium perchlorate.

14. The method of claim 13 wherein said first and second potential values are approximately 0.0 V to 1.5 V.

15. The method of claim 1 wherein said step of measuring and recording current includes the step of comparing said current to a standardized scale to estimate the continued usability of said supply.

16. The method of claim 1 further comprising the steps of:

varying the potential from the second value to the first value to produce a reduction reaction in at least some of said portion of said oxidation products; and measuring and recording the current during said reduction reaction.

17. The method of claim 1 wherein:

said step of bringing electrodes into contact with a sample is preceded by the step of obtaining at least one sample from at least one supply of material of known freshness; and said step of measuring and recording includes producing at least one reference value from said at least one sample.

18. The method of claim 17 wherein said freshness is defined by time and temperature parameters.

19. The method of claim 17 wherein said step of obtaining at least one sample is preceded by the step of simulating the aging of at least one supply of material to simulate a level of known freshness therein.

20. The method of claim 19 wherein said step of simulating the aging of at least one supply of material comprises:

increasing the temperature of a supply of material above its normal storage temperature; and maintaining an increased temperature for at least one predetermined period of time to increase the rate of oxidative degradation in said material;

thereby simulating the aging of said material to a level of known freshness.

21. The method of claim 1 wherein said method includes the step of substantially dissolving a portion of said supply of material, including said aldehyde and phenol oxidation products in a solvent, to prepare a sample.

22. The method of claim 21 wherein the ratio by volume of said solvent to said portion of said supply of material in said sample is greater than 1 to 1.

23. The method of claim 21 wherein said step of substantially dissolving a portion of said material, comprises preparing said sample as an electrically conductive, basic solution.

24. A method for measuring the freshness and stability of a supply of material subject to oxidative degradation, wherein said supply of material subject to oxidative degradation is selected from the group consisting of fuels, food products, animal products, and plant products, said group excluding lubricants, lubricating oils, and cooking oils, said method comprising the steps of:

substantially dissolving material from said supply in a solvent in which the oxidation products of said material are also soluble, to produce a sample;

bringing electrodes into contact with said sample of material from a supply subject to oxidative degradation to measure the oxidation products of the material;

applying an electric potential of a first value to the sample to produce an electric current therethrough;

varying the potential in a single sweep from the first value to a second value to produce an oxidation reaction in at least a portion of said oxidation products; and measuring and recording the current during said oxidation reaction.

* * * * *